United States Patent [19]

Nunberg et al.

[11] Patent Number: 4,818,769
[45] Date of Patent: Apr. 4, 1989

[54] METHOD OF CONTROLLING STRESS-RELATED DISEASE IN LIVESTOCK BY ADMINISTRATION OF HUMAN IL-2

[75] Inventors: Jack H. Nunberg; Michael Doyle, both of Oakland; Arthur Newell, Orinda; Thomas White, Oakland, all of Calif.

[73] Assignee: Cetus Corporation, Emeryville, Calif.

[21] Appl. No.: 856,680

[22] Filed: Apr. 25, 1986

Related U.S. Application Data

[63] Continuation-in-part of Ser. No. 778,371, Sep. 20, 1985, abandoned.

[51] Int. Cl.$^4$ ............................................. A61K 37/02
[52] U.S. Cl. ............................................. 514/2; 514/12
[58] Field of Search ..................................... 514/2, 12

[56] References Cited

U.S. PATENT DOCUMENTS

| | | | |
|---|---|---|---|
| 4,053,593 | 10/1977 | Frumoff | 514/8 |
| 4,518,584 | 5/1985 | Mark et al. | |
| 4,571,336 | 2/1986 | Houck et al. | 514/2 |
| 4,588,585 | 5/1986 | Mark et al. | 514/8 |
| 4,604,377 | 8/1986 | Fernandes et al. | 514/8 |

FOREIGN PATENT DOCUMENTS 0089062  3/1983  European Pat. Off. .

OTHER PUBLICATIONS

Watson, *Immunological Rev.*, 51, 258–272 (1980).
Redelman, *J. of Immunological Methods*, 56, 359–370 (1983).
Ruscetti, *Blood*, 57, No. 3, 379–394 (1981).
Carter, *Fed. Proceedings*, 44, No. 4, 1290 (1985), abst. No. 5141.
Stotter, *Eur. J. Immunol.*, 10, 719–722 (1980).
Reed, *The Journal of Immunology*, 133, No. 6, 3333–3337 (1984).
Farrar, *Immunological Rev.*, 63, 158–160 (1982).
Doyle, *J. of Biological Response Modifiers*, 4, 96–109 (1985).
Yoshimoto, *Chemical Abstracts*, 99, 604 (1983), Abst. No. 193057z.
Sukhih, et al., Dokl Akad Nauk USSR, 278 (3):762-5 (1984).
*The Merck Index*, 9th Ed., Merck & Co., Inc. Rahway, N.J., U.S.A. 1976, entry 7349.

*Primary Examiner*—Johnnie R. Brown
*Assistant Examiner*—F. T. Moezie
*Attorney, Agent, or Firm*—Albert P. Halluin; Dianne E. Reed; Philip L. McGarrigle

[57] ABSTRACT

Disclosed herein is a method of mitigating stress-related syndromes in livestock, such as shipping fever in cattle, by administration of human IL-2.

6 Claims, 3 Drawing Sheets

```
                         5                  10                 15                 20
       AlaProThrSerSer  SerThrLysLysThr  GlnLeuGlnLeuGlu  HisLeuGlnLeuAsp
                        25                 30                 35                 40
       LeuGlnMetIleLeu  AsnGlyIleAsnAsn  TyrLysAsnProLys  LeuThrArgMetLeu
                        45                 50                 55                 60
       ThrPheLysPheTyr  MetProLysLysAla  ThrGluLeuLysHis  LeuGlnCysLeuGlu
                        65                 70                 75                 80
       GluGluLeuLysPro  LeuGluGluValLeu  AsnLeuAlaGlnSer  LysAsnPheHisLeu
                        85                 90                 95                 100
       ArgProArgAspLeu  IleSerAsnIleAsn  ValIleValLeuGlu  LeuLysGlySerGlu
                        105                110                115                120
       ThrThrPheMetCys  GluTyrAlaAspGlu  ThrAlaThrIleVal  GluPheLeuAsnArg
                        125                130                135                140
       TrpIleThrPheCys  GlnSerIleIleSer  ThrLeuThr----
```

FIG. 1

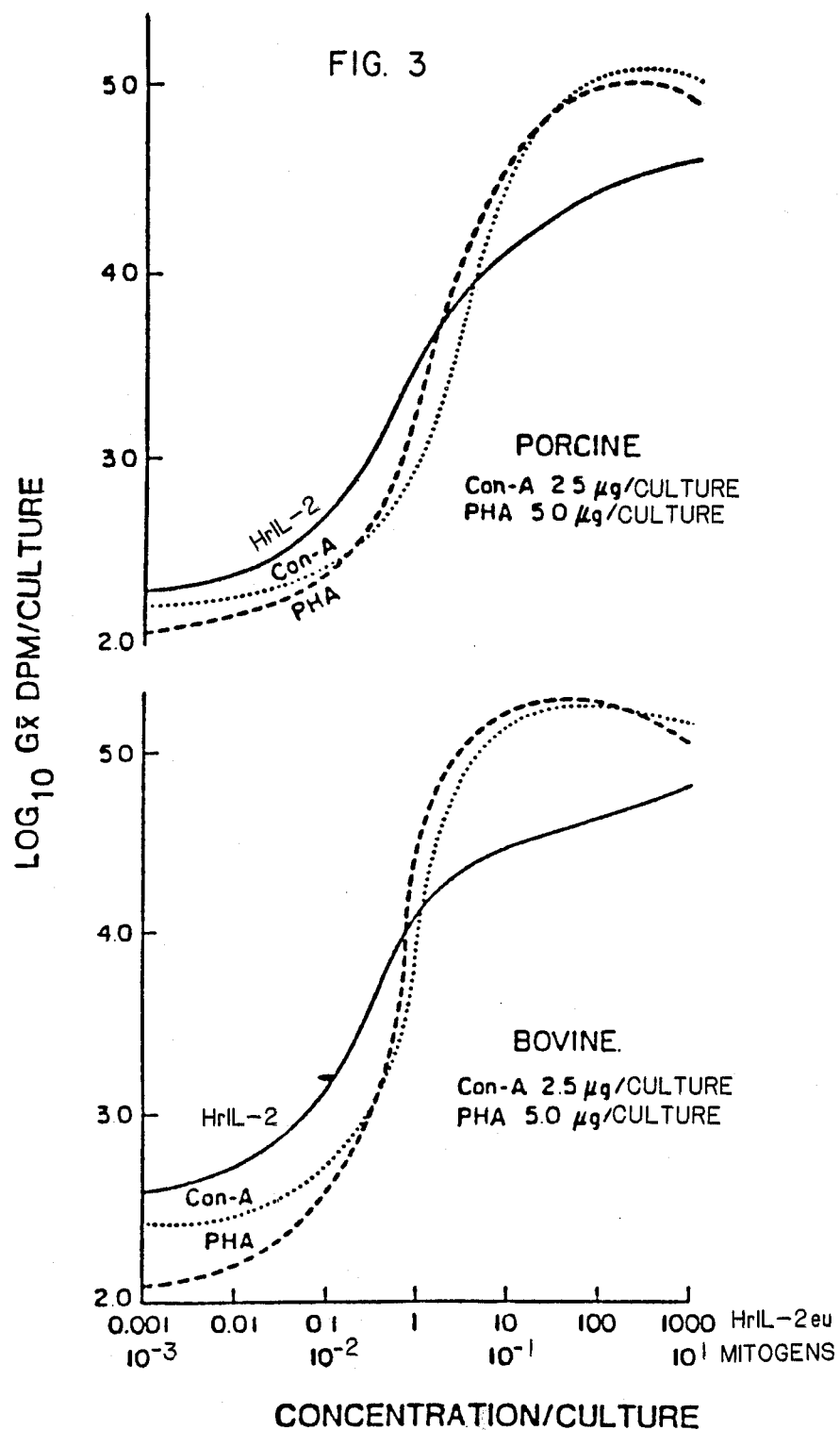

METHOD OF CONTROLLING STRESS-RELATED DISEASE IN LIVESTOCK BY ADMINISTRATION OF HUMAN IL-2

CROSS-REFERENCE TO RELATED APPLICATION

This application is a continuation-in-part of copending U.S. patent application Ser. No. 778,371, filed Sept. 20, 1985, now abandoned.

DESCRIPTION

Technical Field

The invention relates to the prevention and amelioration in animals of symptoms of the malaise associated with livestock animals on feedlots, a symptomatology commonly known as "shipping fever". More particularly, the invention relates to a method of preventing or moderating the disease-potentiating effects of stress and viral infection in animals by administration of human interleukin-2 (hIL-2), including recombinantly produced hIL-2.

Background

Livestock food animals, particularly cattle, are adversely affected by shipment and feedlot conditions, which involve stress from overcrowding, weaning, transport, sometimes severe weather, and, in general, a non-natural environment. One syndrome, commonly known as "shipping fever", is sometimes also designated "bovine respiratory disease syndrome", or BRDS. It is a complex of disease symptoms rather than a specific disease, and is characterized by immune suppression and propensity to succumb to infection by one or more viral, or bacterial pathogens.

Other animals are also subject to adverse reactions to stress. For example, pigs, while ordinarily not shipped in the manner of cattle, can suffer negative respiratory reactions to weaning or just to poor weather. Again, the symptomatology does not lend itself to experimental models. No general treatment for stress-related disorders in livestock has been found. Sick animals are typically treated with antibiotics. Recently several commercial entities have offered interferon preparations for treating shipping fever.

There is considerable background information available with respect to the biological activity of hIL-2. IL-2 is obtained from the supernatant of concanavlin-A (ConA) stimulated spleen cells or, presently, using recombinant technology, and has several measurable activities in vitro. First, it is a T-cell growth factor as measured by, for example, thymidine uptake when IL-2 is added to cultures of cytotoxic or helper T-cell lines. It is mitogenic with respect to adult thymocytes, and stimulates a cytotoxic cell response (e.g., lymphokine-activated-killer (LAK) cell). It has also been shown to replace helper T-cells in athymic murine spleen cell cultures (Watson, J., et al, *Immunological Rev* (1980) 51:257–278). Specifically, in the presence of IL-2 and antigen, specific T helper cells are generated which are able to contribute to antibody responses. Presumably this occurs because IL-2 is involved in the antigen-dependent maturation of helper T-cells in these nude mouse spleen cultures.

IL-2 has also been shown to directly affect B cells in vitro. Both proliferation and IgM and IgG secretion are enhanced by IL-2 in populations of purified, activated B cells (Mingari, M.C., et al., *Nature* (1984) 312:641; Mittler, R., et al., *J. Immunol.* (1985) 134: 2393–2399; Muraguchi, A., et al., *J. Exp. Med.* (1985) 161:181–197).

How these in vitro activities translate into a specific in vivo mechanism for mounting an immune defense is not clear. However, with respect to such in vitro studies, cross-reactivity among species of various IL-2s has been studied. For example, Redelman, D., et al, *J Immunol Meth* (1983) 56:359–370) show that hIL-2 supports activated T lymphocytes derived from rabbit and mouse to approximately the same extent as they are supported by the endogenous forms of IL-2. Ruscetti, F. W., et al, *Blood* (1981) 57:379–393 were the first to demonstrate the ability of hIL-2 to behave as a growth factor, not only for human T-cells, but also peripheral blood lymphocytes or splenocytes from other primates, horse, guinea pig, cat, rat, and mouse. Carter, J., et al (*Fed Proc* (1985) 44:1290) disclose the ability of hIL-2 to enhance the development and maintenance of bovine cytotoxic lymphocytes in vitro.

Doyle, M. V., et al, *J Bio Resp Mod* (1985) 4:96–109 reports in vitro lymphocyte proliferation studies that compared the activities of native hIL-2 and a recombinant form of IL-2 on human and animal lymphocytes. The native IL-2 and recombinant IL-2 exhibited the same range of activity on animal cells.

Some in vivo data are also available. The activity of IL-2 in vivo has been shown to restore immunocompetence in nude mice in response to heterologous erythrocytes (Stotter, H., et al. *Eur J Immunol* (1980) 10:719–722). There is some information concerning cross-species reactivity, as well. Reed, S. G., et al, *J Immunol* (1984) 133:3333, disclosed the ability of hIL-2 to reconstitute spleen cell responses in mice infected with a parasitic protozoan, and Farrar, J. J., et al, *Immunol Rev* (1982) 63:158, showed that in vivo injection of IL-2 of human origin stimulates the splenic T-cells in nude mice.

In summary, it is known that IL-2 behaves in some manner in vivo to mediate a successful immune response, including a response to a specific antigen, and in vitro studies have shown that cross-species reactivity of hIL-2 is very diverse (prior in vivo crossspecies studies have involved only murine subjects for hIL-2). However, because the mechanism of involvement of IL-2 in the immune response is not understood, it is not possible to predict the behavior of IL-2 in boosting an immune response to prevent or ameliorate a particular disease or to predict its overall effect. Accordingly, there is no suggestion in the art that IL-2, and in particular hIL-2, would successfully mitigate the incidence of shipping fever or other stressrelated syndromes that affect livestock. This is the contribution of the present invention.

DISCLOSURE OF THE INVENTION

The invention provides a practical approach to controlling a poorly defined disease that affects an estimated 12 million cattle per year in the United States alone, resulting in a half million deaths among young cattle with the concomitant waste in food supplies. The symptomatology associated with shipping and feedlot cultivation of these cattle can be controlled using hIL-2, including the recombinant forms thereof. In addition, all livestock suffer from characteristic adverse infection-related reactions to stress, and exhibit poorly defined symptomatologies which are similarly treatable. By utilizing the available recombinant forms, a supply of effective hIL-2 is made available in practical amounts and at relatively low cost.

In one aspect, the invention relates to methods of controlling (i.e., prophylaxis or amelioration of severity or duration) shipping fever or other adverse reactions to stress in livestock by administration of an effective dose of hIL-2, including that recombinantly produced. In other aspects, the invention relates to symptomatolytic formulations of hIL-2 for controlling such stress-related symptoms.

BRIEF DESCRIPTION OF THE DRAWINGS

FIG. 1 shows the amino acid sequence of native hIL-2.

FIG. 3 shows the effect of hIL-2 on blastogenesis of bovine and porcine T-lymphocytes.

MODES OF CARRYING OUT THE INVENTION

A. Definitions

Figure 2A:
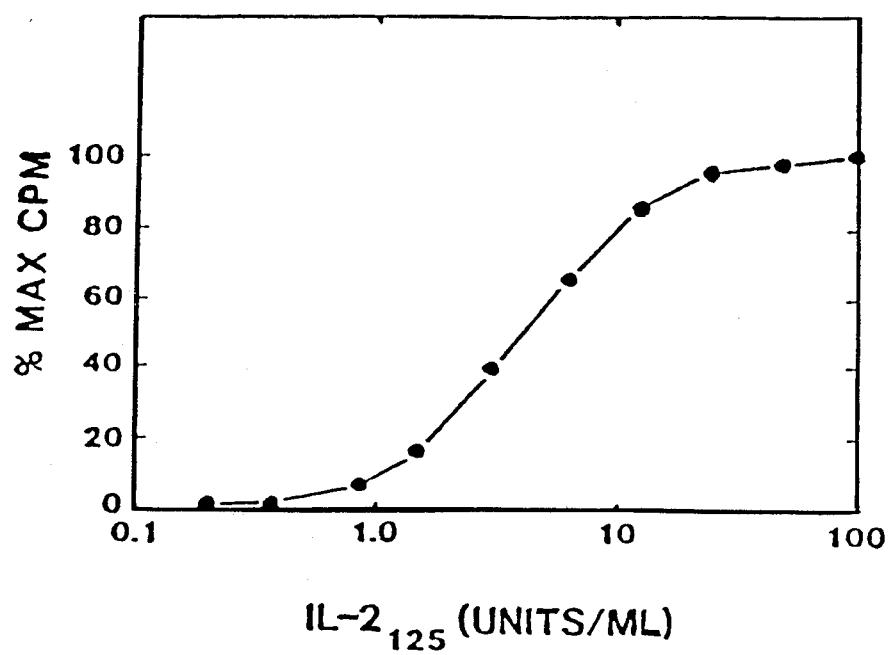
FIGS. 2A and 2B are dose-response curves showing the results of the lymphocyte proliferation tests described in section C.1 of the examples, infra.

As used herein, "hIL-2" refers to a polypeptide exhibiting the spectrum of activities characterizing this protein. Specifically, the protein must be capable of stimulating the proliferation of hIL-2 dependent cytolytic and helper T cell lines, as set forth in the standard assays of Gillis, S, et al, *J Immunol* (1978) 120:2027–2032 and of Watson, J. *J Exp Med* (1979) 150:1510–1519. The amino acid sequence of native hIL-2 is shown in FIG. 1. This primary amino acid sequence may be obtained as the native protein from natural sources or may be recombinantly derived. Other primary sequences of modest modification including deletion, addition, substitution or alterations of the amino acids of the sequence shown, which do not result in serious impairment of activity are, of course, included in the definition. For example, it is established that replacement of the cysteine at position 125 with a neutral amino acid results in a mutein of superior stability and satisfactory reactivity. (See U.S. Pat. No. 4,518,584; Doyle, M.V., et al, supra.)

In addition, IL-2, like any other protein, may exist in neutral or in salt form, and may contain associated nonprotein materials in the nature of glycosylation, phosphorylation, or acetylation. These modifications, too, are included in the definition so long as biological activity is not destroyed thereby.

As used herein the term "stress-induced syndrome" refers to a state of immunosuppression in which an animal has a propensity to succumb to infection by one or more bacterial or viral pathogens, lose weight, or exhibit general ill health.

"Shipping fever" or "bovine respiratory disease syndrome" (BRDS) is defined as negative symptomatology including depression, immunosuppression, weight loss, respiratory problems, viral or bacterial infection, and general ill health and death which are associated with the transportation of cattle to, and the maintenance of cattle on, feedlots. The disease is defined in terms of epidemiology rather than in terms of a model which describes the course of an infection or specific set of metabolic parameters. The criterion for effectiveness against this disease is the maintenance of healthy animals faced with the specific conditions associated with shipping stress and feedlot maintenance.

However, certain parameters of the disease are recognized. It is characterized by an abrupt onset, usually within two weeks of stress, and the symptoms may include dyspnea, cough, ocular and nasal discharge, inappetance and rapid weight loss, fever, increased lung sounds, and general depression. Various bacteria and viral cultures have been isolated from affected animals, including *Pasteurella spp. Haemophilus spp.* infectious bovine rhinotracheitis, parainfluenza-3 virus, and bovine respiratory syncytial virus. The disease typically affects 40–50% of exposed animals and the resulting deaths are typically 2–5% of the exposed population.

B. General Method

The formulations of the invention are most conveniently administered by intramuscular injections or as sustained release compositions although other methods of administration are possible. Specific formulations to prevent hydrolysis during digestion would be necessitated for oral formulation, and intravenous injections are generally uneconomic due to the skill level and care required in the administration. Therefore, formulations suitable for intramuscular injection, expecially sustained release formulations, are preferred.

Standard formulations are either liquid injectables or solids which can be taken up in suitable liquids as suspensions or solutions for injection. Suitable excipients are, for example, water, saline, dextrose, glycerol, ethanol, and so forth. Nontoxic auxiliary substances, such as wetting agents, buffers, or emulsifiers may also be added. One specific useful formulation contains an effective amount of detergent, such as 0.1% sodium dodecyl sulfate (SDS), to effect solubility and bacteriostasis. A variety of techniques may be used to effect long-term stability and slow release. For example, stability is enhanced by coupling to a homopolymer such as polyethylene glycol (PEG). As described in copending commonly owned U.S. patent application Ser. No. 749,955, filed June 26, 1985, and incorporated herein by reference, proteins . . . are covalently bonded via one or two of the amino acid residues of the proteins, depending mainly on the reaction conditions and the particular protein employed. While the residues may be any reactive amino acids on the portein, such as one or two cysteines with reactive thiol groups to form a thiol ester linkage or N-terminal amino acid groups such as proline on IL-2, which proline may react when higher levels of modification are employed, preferably the reactive amino acid is lysine, which is linked to the reactive group of the activated polymer through its free $\epsilon$-amino group.

The homopolymer to which the protein is attached is a homopolymer of polyethylene glycol (PEG) or polypropylene glycol (PPG), each of which must have a molecular weight between about 500 and 20,000, preferably between 2,000 and 10,000, depending on the particular protein employed. In addition, the homopolymer must have a straight chain so as not to render the protein immunogenic. Therefore, preferably the homopolymer is unsubstituted, but it may also be substituted at one end with an alkyl group containing one carbon atom in its chain. This signifies that one terminal OH group of the glycol is replaced by an O-alkyl group. Preferably the alkyl group is a $C_1$–$C_4$ alkyl group, and most preferably a methyl group, to prevent crosslinking reactions. Most preferably, the homopolymer is monomethyl-substituted PEG with a molecular weight of 2,000 to 10,000.

The IL-2 is linked to the homopolymer via a coupling agent, which must have reactive groups which will selectively react with free amino or other reactive groups on the protein. For IL-2 the amount of homopolymer employed is preferably no more than 50 moles per mole of IL-2, and most preferably is about 5 to 20 moles per mole of IL-2, depending on the specific properties ultimately desired, i.e., the final amount is a balance to maintain optimum activity, while at the same time maximizing, if possible, the half-life of the protein. Preferably, at least about 50% of the biological activity of the protein is retained, and most preferably 100% is retained.

The covalent coupling reaction may take place by any suitable method generally used for coupling between biologically active materials and inert polymers, provided that it take place at a pH of 8 to 10, preferably about 9.0, if the reactive groups on the protein are lysine groups. Use of pH values lower than 8 for the lysine reaction may result in decreased modification of the protein. Generally the process involves reacting at least one terminal hydroxyl group of the homopolymer with a coupling agent to provide an activated polymer, and thereafter reacting the protein with the activated polymer to produce the solubilized protein suitable for formulation.

The above coupling reaction can be performed by several methods, which may involve one or more steps. Examples of suitable coupling agents which can be used in a one-step reaction include cyanuric acid chloride (2,4,6-trichloro-S-triazine) and cyanuric acid fluoride.

In a preferred embodiment the reaction takes place in two steps wherein the homopolymer is reacted first with an acid anhydride such as succinic or glutaric anhydride to form a carboxylic acid, and the carboxylic acid is then reacted with a compound capable of reacting with the carboxylic acid to form an activated polymer with a reactive ester group which is capable of reacting with the protein. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted in the presence of a mild base with succinic anhydride. The monomethyl PEG-succinic acid thus produced is then reacted with N-hydroxysuccinimide in the presence of a carbodiimide reagent such as dicyclohexyl or isopropyl carboiimide to produce the activated polymer, methoxypolyethylene glycolyl-N-succinimidyl succinate, which can then be reacted with the protein. This method is described in detail in Abuchowski et al., *Cancer Biochem. Biophys.*, 7, 175-186 (1984). In another example the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described in Bhatnagar et al., *Peptides: Synthesis-Structure-Function, Proceedings of the Seventh American Peptide Symposium*, Rich, et al. (eds.) (Pierce Chemical Co., Rockford IL, 1981), p. 97-100, and in Nitecki et al., *High-Technology Rooute to Virus Vaccines* (American Society for Microbiology, anticipated Fall 1985--in press), entitled "Novel Agent for Coupling Synthetic Peptides to Carriers and Its Application."

This PEG-hIL-2 complex, called "PEGylated" hIL-2, is particularly useful for administering a single sustained action dose of hIL-2.

As described in U.S. patent application Ser. No. 749,955, the PEGylated hIL-2 complex is formed by covalent bonding of the IL-2 via one or two amino acid residues. While the residues may be any reactive amino acids on the protein, such as one or two cysteines with reactive thiol groups to form a thiol ester linkage or N-terminal amino acid groups, the reactive amino acid is preferably lysine, which is linked to polyethylene glycol through its free epsilon-amino group.

The polyethylene glycol to which the IL-2 is coupled has a molecular weight between about 500 and 20,000, preferably between 2,000 and 10,000. In addition, the PEG must have a straight chain so as not to render the protein immunogenic. Thus, the PEG is preferably unsubstituted, but may be substituted at one end with an alkyl group containing one carbon atom in its chain. This signifies that one terminal OH group of the glycol is replaced by an O-alkyl group. Preferably the alkyl group is a $C_1$-$C_4$ alkyl group, and most preferably a methyl group, to prevent crosslinking reactions. Most preferably, the PEG is monomethyl-substituted PEG with a molecular weight of 2,000 to 10,000.

The IL-2 is linked to the PEG via a coupling agent, which must have reactive groups which will selectively react with free amino or other reactive groups on the protein. It is recommended that generally the amount of PEG employed is preferably no more than 50 moles per mole of IL-2, and most preferably is about 5 to 20 moles per mole of IL-2, depending on the specific properties ultimately desired, i.e. the final amount is a balance to maintain optimum activity, while at the same time maximizing, if possible, the half-life of the IL-2. Preferably, at least about 50% of the biological activity of the IL-2 is retained, and most preferably 100% is retained.

The covalent coupling reaction may take place by any suitable method generally used for coupling between biologically active materials and inert polymers, provided that it takes place at a pH of 8 to 10, preferably about 9.0, if the reactive groups on the protein are lysine groups. Use of pH values lower than 8 for the lysine reaction may result in decreased modification of the IL-2. Generally the process involves reacting at least one terminal hydroxyl group of the PEG with a coupling agent to provide an activated polymer, and thereafter reacting the IL-2 with the activated polymer to produce the solubilized protein suitable for formulation.

The above coupling reaction can be performed by several methods, which may involve one or more steps. Examples of suitable coupling agents which can be used in a one-step reaction include cyanuric acid chloride (2,4,6-traichloro-S-triazine) and cyanuric acid fluoride.

In a preferred embodiment the reaction takes place in two steps wherein the PEG is reacted first with an acid anhydride such as succinic or glutaric anhydride to form a carboxylic acid, and the carboxylic acid is then reacted with a compound capable of reacting with the carboxylic acid to form an activated polymer with a reactive ester group which is capable of reacting with the protein. Examples of such compounds include N-hydroxysuccinimide, 4-hydroxy-3-nitrobenzene sulfonic acid, and the like, and preferably N-hydroxysuccinimide or 4-hydroxy-3-nitrobenzene is used. For example, monomethyl substituted PEG may be reacted in the presence of a mild base with succinic anhydride. The monomethyl PEG-succinic acid thus produced is then reacted with N-hydroxysuccinimide in the presence of a carbodiimide reagent such as dicyclohexyl or isopropyl carbodiimide to produce the active polymer, methoxypolyethylene glycolyl-N-succinimidyl succinate, which can then be reacted with the protein. This method is described in detail in Abuchowski et al., *Can-* cer Biochem. Biophys., 7, 175–186 (1984). In another example the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described in Bhatnagar et al., Peptides: Synthesis-Structure-Function, Proceedings of the Seventh American Peptide Symposium, Rich et al. (eds.) (Pierce Chemical Co., Rockford, IL 1981), pp. 97–100, and in Nitechki et al., *High Technology Route to Virus Vaccines* (American Society for Microbiology, 1985), entitled "Novel Agent for Coupling Synthetic Peptides to Carriers and Its Application").

Sustained and continuous release formulations are of considerable variety, as is understood by those skilled in the art. An exemplary composition for sustained release parenteral administration is an injectable microcapsule formulation that with a single injection will deliver recombinant hIL-2 or soluble forms of hIL-2, such as PEGylated hIL-2, at a controlled rate of about $10^3$ to $10^5$ units/kg/day for a duration of 14 to 30 days. (Pure hIL-2 has a specific activity of about $3-6 \times 10^6$ u/mg.) The microcapsule formulation is a free-flowing powder consisting of spherical particles 20 to 100 $\mu$m in diameter that can be injected intramuscularly or subcutaneously with a conventional hypodermic needle, and the microcapsules consist of 0.5 to 5% hIL-2 encapsulated in poly(DL-lactide-co-glyco lide) (DL-PLG) excipient, a biodegradable, biocompatible polyester. Alternative standard formulations for sustained release are also usable.

The regime of administration for shipping fever will depend on the conditions of shipment and the feedlot. It is preferred that administration be continuous and be begun prior to shipment or at least as early as arrival on the feedlot and be continued over a period of, for example, 14–30 or more days. The term "continuous" is intended to denote true continuous administration, such as is achieved via a sustained release dosage form as well as a multiplicity of intermittent administrations of hIL-2 (or enhanced half-life forms of hIL-2 such as PEGylated hIL-2) that provide a pharmacokinetic pattern that mimics that achieved by true continuous administration. Daily doses in the range of above about $10^3$ and below about $10^6$ units/kg/day, preferably about $10^4$ to $10^5$ units/kg/day, are generally used. In cattle, doses above about $10^6$ units/kg/day began to cause undesirable side effects.

For other livestock stress-induced or respiratory distress syndromes, the regime and amounts administered will depend on the nature and size of the animal (e.g., pig, goat, sheep, etc.) and on the severity of the symptoms. It is likely, however, that the effective dose for such syndromes will be in the same (on a unit weight basis) range as that used for shipping fever.

The hIL-2 may be administered by itself or as a supplement to vaccines used to protect against stress-related diseases.

C. Examples

The following examples are intended to further support or illustrate but not to limit the invention.

C.1. In Vitro Activity

Figure 2B:
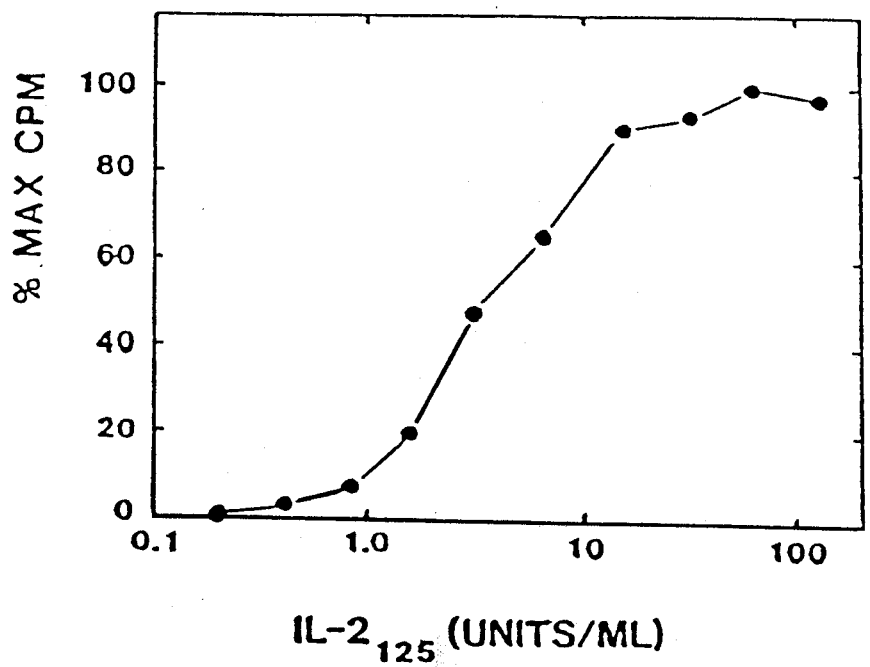

In vitro activity with respect to bovine and porcine peripheral blood mononuclear cells (PBMC) has been shown for recombinant hIL-2 (Fong, Susan, et al, *Vet Immunol and Immunopathol* (1986) 11:91–100 and incorporated herein by reference). The hIL-2 used in this work is designated des-alanyl-rIL-$2_{ser125}$, lacks an initial alanine, and has a serine rather than a cysteine at position 125. It was shown to be mitogenic for unactivated bovine and porcine PBMC, and to be able to maintain the long-term growth of ConA-activated PBMC from both species. FIGS. 2A and 2B are curves showing the dose-response of ConA-activated bovine (2A) and porcine (2B) PBMC to des-alanyl-rIL-$2_{ser125}$. Also, bovine and porcine PBMC preincubated with des-alanyl-rIL-$2_{ser125}$ for 1–5 days showed enhanced cytotoxicity against tumor cell targets.

In addition, Stott, J. L., et al (submitted and incorporated herein by reference) have shown that bovine and porcine peripheral blood lymphocytes were responsive to human recombinant IL-2 in lymphocyte blastogenesis assays. Blastogenesis was determined by incorporation of $^3$H-thymidine (18 hr pulse) in 4-day lymphocyte cultures, and the results expressed as the $\log_{10}$ of the geometric mean ($G_x$) of disintegrations per minute (DPM)/culture and plotted by nonlinear regression analysis as shown in FIG. 3. Mitogen dilution and concentration of hIL-2 in units are shown on the X-axis. These results show that the effect of hIL-2 on bovine and porcine cells is comparable to that shown by the plant lectins PHA and ConA, which are known to stimulate blastogenesis.

C.2. Potentiation of Cell-Mediated Immunity

Since respiratory diseases are predominantly controlled by the cellular (T-cell) immune system, the ability of hIL-2 to boost the cellular immune response in livestock is indicative of its effectiveness against these symptomologies. In vivo injections of recombinant hIL-2 produced elevated levels of lymphocyte blastogenesis in the blood of calves.

Specifically, eight calves weighing 135–225 kg (3–5 months old) were randomly sorted into 4 groups of 2 each which received weekly injections for one month as follows: Groups 1, 2, and 3 received $10^4$, $10^5$, and $10^6$ units/kg, respectively, intramuscularly; group 4 received only excipient. The animals were assessed for lymphocyte stimulation. The results show that resting lymphocyte activity was elevated by the recombinant hIL-2 treatment as determined by blastogenesis assays performed prior to each inoculation over the period in calves receiving $10^5$ and $10^6$ units/kg only. For calves receiving $10^5$ units/kg, lymphocyte activity returned to normal within two weeks following the last IL-2 administration; $10^6$ units/kg-injected calves remained elevated at that time.

C.3. Treatment of Shipping Fever

Two hundred heifers were purchased from several different sources in Tennessee and transported to a research feedlot in Colorado. The average weight of the animals was approximately 400 lbs. The animals were segregated randomly (weight and breed) into four groups, designated I through IV.

Recombinant hIL-2 (des-alanyl-rIL-$2_{ser125}$) was formulated in 0.05% SDS and administered intramuscularly to the animals upon entry to the feedlot. All animals were treated daily, five times per week, for two weeks. The dose protocols for the four groups were as follows.

| Group | IL-2 Dose (u/kg/day) |
|---|---|
| I | $2 \times 10^4$ (high dose) |
| II | $2 \times 10^3$ (mid dose) |
| III | $2 \times 10^2$ (low dose) |

The animals did not receive standard BRDS-related vaccination. They were, by chance, subjected to severe snow and cold weather during their first days on the feedlot, and accordingly, were placed on silage feed early on. The health of the animals was observed on a daily basis by personnel blind to experimental treatment. The animals were weighed at regular intervals. Table 1 reports the results of the treatment as of day 21.

TABLE 1

| | Mortality Number Dead/Total | |
|---|---|---|
| Control | 21/50 | |
| Low Dose | 20/50 | p = 0.839 |
| Mid Dose | 26/50 | p = 0.316 |
| High Dose | 14/50 | p = 0.142 |
| | Incidence of Disease Number Sick or Dead/Total | |
| Control | 43/50 | |
| Low Dose | 42/50 | p = 0.779 |
| Mid Dose | 43/50 | p = 1.000 |
| High Dose | 38/50 | P = 0.202 |
| | Severity of Disease Average Daily Severity Score of Group (Score 0-3; Death = 4) | |
| Control | 1.76 | |
| Low Dose | 1.79 | p = 0.950 |
| Mid Dose | 1.93 | p = 0.395 |
| High Dose | 1.38 | p = 0.052 |

Morbidity and mortality rates during the study were higher than expected. As reported some groups showed 85% morbidity and 50% mortality. Sickness was observed as early as two days into the study. Several factors may have been responsible for the extreme severity of BRDS seen in this study: the severe snow and cold weather; the animals were 'light-weight' (400 lbs avg) and 'thin-skinned' (from Tennessee); groups had been 'put-together' from several sources (thus, they were not 'fresh' and many had seen several salebarns prior to shipping to Colorado); and the animals were placed on silage feed early on, and may have been eating poorly.

In the clinical judgement of the personnel observing the health of the animals, the high-dose IL-2 group consistently "looked better". This is supported by the data in Table 1 in which the high-dose IL-2 group showed a consistent trend towards decreased mortality; decreased incidence of disease; and decreased severity of disease.

In all cases, the high-dose group performed better than the control group. Although the statistical significance of these differences (p-value), is marginal (using the strict definition of p<0.05), all results are consistent.

Additional measures not presented in Table 1 also supported the trend toward efficacy in the highdose IL-2 group. For instance, animals in the high-dose group which died, did so later in the study than did control animals.

As of day 21, there were no differences in the average weight of surviving animals. There were, however, significant differences in the total pay-weight per group, since more animals survived in the high-dose group.

Modifications of the above-described modes for carrying out the invention that are obvious to those of skill in the fields of veterinary medicine, immunology, pharmacology, and related fields are intended to be within the scope of the following claims.

We claim:

1. A method of diminishing the incidence of shipping fever in livestock which comprises administering to subject livestock an amount of a water soluble form of hIL-2 in the range of above about $10^3$ and below about $10^6$ u/kg/day over a period of from about 14 to 30 days, wherein the water soluble form of hIL-2 is hIL-2 covalently bonded through one or two amino acids via a coupling agent to polyethylene glycol having a molecular weight in the range of from about 500 to 200,000, and wherein no more than about 50 moles of polyethylene glycol are employed per mole hIL-2.

2. A method of diminishing the incidence of shipping fever in livestock which comprises administering to subject livestock an amount of a water soluble form of des-alanyl-rIL-$2_{ser125}$ in the range of above about $10^3$ and below about $10^6$ u/kg/day over a period of from about 14 to 30 days, wherein the water soluble form of hIL-2 is hIL-2 covalently bonded through one or two amino acids via a coupling agent to polyethylene glycol having a molecular weight in the range of from about 500 to 200,000, and wherein no more than about 50 moles of polyethylene glycol are employed per mole des-alanyl-rIL-$2_{ser125}$.

3. A method of ameliorating the symptoms of shipping fever in livestock which comprises administering to subject livestock an amount of a water soluble form of hIL-2 in the range of above about $10^3$ and below about $10^6$ u/kg/day over a period of from about 14 to 30 days, wherein the water soluble form of hIL-2 is covalently bonded through one or two amino acids via a coupling agent to polyethylene glycol having a molecular weight in the range of from about 500 to 200,000, and wherein no more than about 50 moles of polyethylene glycol are employed per mole hIL-2.

4. A method of ameliorating the symptoms of shipping fever in livestock which comprises administering to subject livestock an amount of a water soluble form of des-analy-rIL-$2_{ser125}$ in the range of above about $10^3$ and below about $10^6$ u/kg/day over a period of from about 14 to 30 days, wherein the water soluble form of hIL-2 is hIL-2 covalently bonded through one or two amino acids via a coupling agent to polyethylene glycol having a molecular weight in the range of from about 500 to 200,000, and wherein no more than about 50 moles of polyethylene glycol are employed per mole des-alanyl-rIL-$2_{ser125}$.

5. A method of shortening the duration of shipping fever in livestock which comprises administering to subject livestock an amount of a water soluble form of hIL-2 in the range of above about $10^3$ and below about $10^6$ u/kg/day over a period of from about 14 to 30 days, wherein the water soluble form of hIL-2 is covalently bonded through one or two amino acids via a coupling agent to polyethylene glycol having a molecular weight in the range of from about 500 to 200,000, and wherein no more than about 50 moles of polyethylene glycol are employed per mole hIL-2.

6. A method of shortening the duration of shipping fever in livestock which comprises administering to subject livestock an amount of a water soluble form of des-alanyl-rIL-$2_{ser125}$ in the range of above about $10^3$ and below about $10^6$ u/kg/day over a period of from about 14 to 30 days, wherein the water soluble form of hIL-2 is hIL-2 covalently bonded through one or two amino acids via a coupling agent to polyethylene glycol having a molecular weight in the range of from about 500 to 200,000, and wherein no more than about 50 moles of polyethylene glycol are employed per mole des-alanyl-rIL-2$_{ser125}$.

* * * * *